United States Patent [19]

Hawrylenko

[11] Patent Number: 4,668,220
[45] Date of Patent: May 26, 1987

[54] INFUSION PUMP

[75] Inventor: Alexander Hawrylenko, Bottmingen, Switzerland

[73] Assignee: Infors GmbH, Munich, Fed. Rep. of Germany

[21] Appl. No.: 787,427

[22] Filed: Oct. 15, 1985

[30] Foreign Application Priority Data

Oct. 26, 1984 [DE] Fed. Rep. of Germany ....... 3439322

[51] Int. Cl.⁴ .......................... A61M 1/00; A61M 5/20
[52] U.S. Cl. .................................... 604/155; 604/209;
604/131; 604/135; 604/154; 128/DIG. 1
[58] Field of Search ............................ 604/155, 209;
128/DIG. 1; 604/131, 134, 135, 151, 154

[56] References Cited

U.S. PATENT DOCUMENTS

| 1,751,139 | 3/1930 | Feinstein | 604/155 |
| 2,632,445 | 3/1953 | Kas | 604/209 |
| 2,725,877 | 12/1955 | Reiter et al. | 604/135 |
| 4,196,730 | 4/1980 | Wilson | 604/155 |
| 4,267,836 | 5/1981 | Whitney et al. | 604/246 |
| 4,313,439 | 2/1982 | Babb et al. | 604/135 |
| 4,326,517 | 4/1982 | Whitney et al. | 604/155 |
| 4,333,459 | 6/1982 | Becker | 604/135 |
| 4,415,101 | 11/1983 | Shapiro et al. | 604/209 |
| 4,544,369 | 10/1985 | Skakoon et al. | 604/155 |
| 4,563,175 | 1/1986 | La Fond | 604/155 |

FOREIGN PATENT DOCUMENTS

| 2390175 | 1/1979 | France | 604/155 |
| 0016069 | of 1909 | United Kingdom | 604/135 |

Primary Examiner—Stephen C. Pellegrino
Assistant Examiner—John D. Ferros
Attorney, Agent, or Firm—Max Fogiel

[57] ABSTRACT

An infusion pump for controllable long-term injection of solutions from a syringe which can be emptied in a controlled manner for use with medical drugs in large doses. The infusion pump has a holding device for at least one syringe and an actuating device for the piston of the syringe which is connected to an electrical control drive, and an electrical battery for the drive. The actuating device is provided with a storage device for mechanical work acting through a detent member in the sense of the drive. The electrical control drive is adapted to release a retarding device when switched on, and to actuate the retarding device when switched off.

18 Claims, 1 Drawing Figure

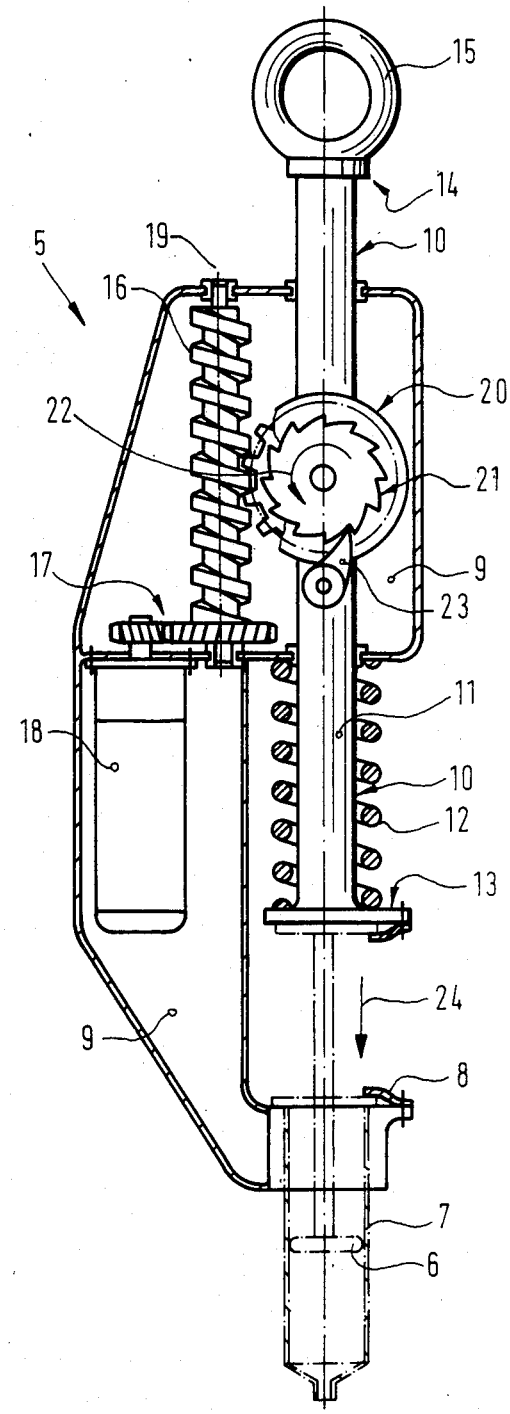

INFUSION PUMP

BACKGROUND OF THE INVENTION

The present invention relates to an infusion pump and more particularly to a pump for the controllable long-term injection of solutions, particularly of medicinal drugs in large doses, from a syringe which can be emptied in a controlled manner. A holding means is provided for at least one syringe, an electrical control drive operating in a driving manner with the actuating device, and an electric battery for the drive.

Such infusion pumps are known in a large number of forms of construction. Apart from a holdiing means for one or more syringes, they comprise, for their emptying, an actuating device which is driven by a mains-operated or battery-operated electric drive. Battery-operated devices have the enormous advantage of greater mobility and readiness for use independently of the mains.

A disadvantage of these known battery-operated infusion pumps is their extremely short operating time which necessitates a frequent and constant charging or changing of the batteries. Furthermore, apart from the operation of the device, it is also necessary to ensure that the batteries are always recharged and are present in sufficient numbers. This makes these known infusion pumps or their operation considerably more expensive, quite apart from the fact that the constant charging or changing of the batteries is a nuisance. In addition, the batteries make the device comparatively heavy. These known infusion pumps have not proved satisfactory in the rough working environment of hospitals or, in particular, mobile invalid vehicles.

SUMMARY OF THE INVENTION

The present invention seeks to provide an infusion pump which is lighter, simpler and less costlier to manufacture so that it has a long operating time.

According to the present invention, there is provided a pump having means for holding a syringe, means for actuating a piston of the syringe, mechanical energy storage means which operate the actuating means via retarding means, and electrical control means which controls the retarding means.

The present invention is based on providing the energy necessary for the operation of all parts of the infusion pump in the form of, for example, stored mechanical, pneumatic or other non-electrical work or energy which is produced manually, for example by winding up a spring mechanism, tensioning a spring or the like, before the infusion pump is used. The energy of the storage device acts on the actual actuating device for the piston of the syringe through a detent of retarding means, for example through self-locking worm teeth, which are adjusted so that the retardation only just occurs.

The electrical control drive device which, in a preferred form of embodiment is constructed in the form of a direct-current electric motor, has a releasing action on the retarding means when switched on and a re-activating action on the retarding means when switched off, for which purpose—with the appropriately correct dimensioning—the electrical drive device practically only has to work under no load. This implies only extremely low energy requirements which results in a comparatively long operating time. A pulse control device may be provided for the electric drive.

Thus with a normal battery of 2 AH and a consumption of the electrical drive of 9 mA, a running time of 225 h is expected. Assuming an infusion rate of about 5 ml/h, this corresponds to an operating time of about 1500 h in contrast to an operating time of 3 h with an infusion pump of the same type according to the prior art.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

A diagrammatic cross-section through an infusion pump according to the present invention.

DESCRIPTION OF THE PREFERRED EMBODIMENTS

Referring to the drawing, there is shown an infusion pump, designated generally by 5, for a syringe 7 to be emptied by a piston 6. The syringe 7 is detachably located on the housing, designated generally by 9, by a holding device 8. The piston 6 of the syringe 7 is actuated in the direction 24 by an actuating device constructed in the form of a rod 10, under the force of a helical spring 12 surrounding the end 11 of the rod 10 emerging from the housing 9. The spring is supported, on the one hand, on the housing 9, and, on the other hand, on the end 13 of the rod 10 adjacent to the piston. Provided at the free end 14 of the rod 10, emerging at the other side of the housing 9, is a handle which is constructed in the form of a ring 15. The spring 12 can be tensioned by ring 15 when a syringe with a piston is filled on the holding device 8 or is fitted in the already filled state.

A worm 16 is mounted for rotation parallel to the rod 10 and is in driving connection, through spur gearing 17, with an electrical control drive constructed in the form of an electric motor 18. The motor 18 may be constructed in the form of a geared motor. The motor 18 preferably comprises a start-stop control and, when stopped, does not use current. The electric battery and the actuating circuit for the electric motor 18 are not illustrated in the drawing for reasons of clarity and because they are known per se.

Mounted for rotation on the rod 10, perpendicular to the axis of rotation 19 of the worm 16, is a worm wheel 20 which is in meshing engagement with the worm 16 as a retarding device. The selection of the materials of the bearing arrangement and of the teeth and their pitch are such that all the friction which occurs is almost completely overcome by the energy of the spring 12. The worm has a self-locking behavior with static friction and a free-running behavior with sliding friction.

Connected to the worm wheel 20 for rotation therewith but not in relation thereto, is a ratchet wheel 21 which permits free running only in the one direction of rotation 22. This permits the tensioning of the helical spring 12. The ratchet co-operates with a spring-loaded pawl 23 which, in turn, is disposed on the rod 10. The ratchet wheel 21 with the pawl 23 prevents the syringe 7 from being emptied directly through the force of the helical spring 12 as a result of the actuation of its piston 6 in the direction 24, after tensioning of the helical spring 12 by actuation of the rod 10 through the ring 15. After the tensioning, this actuation is only possible if the worm wheel 20 is moved in the pushing direction 24 by turning of the worm 16 by the electric motor 18 along the axis of rotation 19. The pawl 23 may be releasable from outside the housing 9.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

What is claimed is:

1. An infusion pump for controllable long-term injection of solutions from a syringe, comprising: holding means for at least one syringe with a piston; actuating means for said piston of the syringe; electrical control drive means cooperating with said actuating means and having an electric battery for driving; retarding means connected to said actuating means; storage means for storing mechanical work acting on said actuating means through said retarding means in direction of said drive means; said electrical control drive means releasing said retarding means when switched on and actuating said retarding means when switched off, said electrical control drive means having an electric motor running under idling condition when in operative state, said motor experiencing a load condition only for a substantially brief interval when said motor is switched on, said motor providing energy for maintaining said pump in operation upon functional failure of said storage means, said motor operating under power in non-idling condition after failure of said storage means to reduce time of operation, a change in operating condition from idling to non-idling of said motor indicating failure of said storage means; said electric motor comprising a start-stop control, said motor having no current when stopped; said actuating means comprising a rod having a handle at a free end thereof; a housing for said pump; said rod having a metal region guided in said housing, one end of said rod having said handle and the other end of said rod actuating said piston of said syringe; said rod communicating with said storage means and said retarding means; said storage means comprising a spring; a worm wheel with a periphery driven by said electrical control drive means and having worm teeth on the periphery of said worm wheel, said electrical control drive means connected to said actuating means driving through said worm teeth; said worm wheel being parallel to said rod; a worm gear in mesh with said worm wheel and having an axis of rotation perpendicular to the axis of said rod and said worm wheel; said worm wheel having a pitch so that said worm wheel is self-locking for static friction and is free-running for sliding friction; said worm gear having free-wheeling action only in one direction of rotation which determines the pulling of said storage means, said worm gear being locked in the other direction of rotation; said worm gear having a ratchet wheel connected thereto and rotating with said worm gear; a spring-loaded pawl engaging said ratchet wheel; said pawl being releasable from outside said housing.

2. An infusion pump for controllable long-term injection of solutions from a syringe, comprising: holding means for at least one syringe with a piston; actuating means for said piston of the syringe; electrical control drive means cooperating with said actuating means and having an electric battery for driving; retarding means connected to said actuating means; storage means for storing mechanical work acting on said actuating means through said retarding means in direction of said drive means; said electrical control drive means releasing said retarding means when switched on and actuating said retarding means when switched off, said electrical control drive means having an electric motor running under idling condition when in operating state, said motor experiencing a load condition only for a substantially brief interval when said motor is switched on, said motor providing energy for maintaining said pump in operation upon functional failure of said storage means, said motor operating under power in non-idling condition after said failure of said storage means to reduce time of operation, a change in operating condition from idling to non-idling of said motor indicating failure of said storage means; said actuating means comprising a rod; a worm wheel with a periphery driven by said electrical control drive means and having worm teeth on the periphery of said worm wheel, said electrical control drive means connected to said actuating means driving through said worm teeth; said worm teeth being parallel to said rod; and a worm gear in mesh with said worm wheel and having an axis of rotation perpendicular to the axis of said rod and said worm wheel; said worm wheel having a pitch so that said worm wheel is self-locking for static friction and is free-running for sliding friction; said worm gear having free-wheeling action only in one direction of rotation which determines the pulling of said storage means, and is locked in the other direction of rotation; said worm gear having a ratchet wheel connected thereto and rotating with said worm gear; and a spring-loaded pawl engaging said ratchet wheel.

3. An infusion pump for controllable long term injection of solutions from a syringe, comprising: holding means for a least one syringe with a piston; actuating means for said piston of the syringe; electrical control drive means cooperating with said actuating means and having an electric battery for driving; retarding means connected to said actuating means; storage means for storing mechanical work acting on said actuating means through said retarding means in direction of said drive means; said electrical control drive means releasing said retarding means when switched on and actuating said retarding means when switched off, said electrical control drive means having an electric motor running under idling condition when in operative state, said motor experiencing a load condition only for a substantially brief interval when said motor is switched on, said motor providing energy for maintaining said pump in operation upon functional failure of said storage means, said motor operating under power in non-idling condition after said failure of said storage means to reduce time of operation, a change in operating condition from idling to non-idling of said motor indicating failure of said storage means; a worm wheel with a periphery driven by said electrical control drive means and having worm teeth on the periphery, said electrical control drive means connected to said actuating means driving through said worm teeth.

4. An infusion pump for controllable long term injection of solutions from a syringe, comprising: holding means for a least one syringe with a piston; actuating means for said piston of the syringe; electrical control drive means cooperating with said actuating means and having an electric battery for driving; retarding means connected to said actuating means; storage means for storing mechanical work acting on said actuating means through said retarding means in direction of said drive means; said electrical control drive means releasing said retarding means when switched on and actuating said retarding means when switched off, said electrical control drive means having an electric motor running under idling condition when in operative state, said motor experiencing a load condition only for a substantially brief interval when said motor is switched on, said motor providing energy for maintaining said pump in operation upon functional failure of said storage means, said motor operating under power in non-idling condition after said failure of said storage means to reduce time of operation, a change in operating condition from idling to non-idling of said motor indicating failure of said storage means; said actuating means comprising a rod; a worm wheel with a periphery driven by said electrical control drive means and having worm teeth on the periphery; said electrical control drive means connected to said actuating means driving through said worm teeth; said worm wheel being parallel to said rod; and a worm gear in mesh with said worm wheel and having an axis of rotation perpendicular to the axis of said rod and said worm wheel.

5. A pump as defined in claim 4, wherein said worm wheel has a pitch so that said worm wheel is self-locking for static friction and is free-running for sliding friction.

6. A pump as defined in claim 5, wherein said worm gear has free-wheeling action only in one direction of rotation which determines the pulling of said storage means, and is locked in the other direction of rotation.

7. A pump as defined in claim 6, wherein said worm gear has a ratchet wheel connected thereto and rotating with said worm gear; and a spring-loaded pawl engaging said ratchet wheel.

8. A pump as defined in claim 7, wherein said pawl is releasable from outside a housing of said pump.

9. An infusion pump for controllable long-term injection of solutions from a syringe, comprising: holding means for at least one syringe with a piston; actuating means for said piston of the syringe; electrical control drive means cooperating with said actuating means and having an electric battery for driving; retarding means connected to said actuating means; storage means for storing mechanical work acting on said actuating means through said retarding means in direction of said drive means; said electrical control drive means releasing said retarding means when switched on and actuating said retarding means when switched off, said electrical control drive means having an electric motor running under idling condition when in operative state, said motor experiencing a load condition only for a substantially brief interval when said motor is switched on, said motor having means providing energy for maintaining said pump in operation upon functional failure of said storage means, said motor having means operating under power in non-idling condition after said failure of said storage means to reduce time of operation, a change in operating condition from idling to non-idling of said motor indicating failure of said storage means.

10. A pump as defined in claim 9, wherein said electric motor comprises further a direct-current motor.

11. A pump as defined in claim 9, wherein said electric motor comprises a geared motor.

12. A pump as defined in claim 11, wherein said electric motor comprises a start-stop control, said motor having no current when stopped.

13. A pump as defined in claim 9, wherein said actuating means comprises a rod.

14. A pump as defined in claim 13, wherein said rod has a handle at its free end.

15. A pump as defined in claim 13, including a housing of said pump; said rod having a middle region guided in said housing of said pump, one end of said rod having a handle and the other end of said rod actuating said piston of said syringe.

16. A pump as defined in claim 13, wherein said rod communicates with said storage means and said retarding means.

17. A pump as defined in claim 9, wherein said storage means comprises a spring.

18. A pump as defined in claim 9, wherein said electrical control drive means comprises pulse control means.

* * * * *